United States Patent [19]
Dumoulin et al.

[11] Patent Number: 5,713,359
[45] Date of Patent: Feb. 3, 1998

[54] MAGNETIC RESONANCE (MR) PERFUSION IMAGING IN A LOW-FIELD IMAGING MAGNET

[75] Inventors: Charles Lucian Dumoulin, Ballston Lake, N.Y.; Steven Peter Souza, Williamstown, Mass.

[73] Assignee: General Electric Company, Schenectady, N.Y.

[21] Appl. No.: 537,575

[22] Filed: Oct. 2, 1995

[51] Int. Cl.$^6$ .................................................. A61B 5/055
[52] U.S. Cl. ........................... 128/653.2; 128/653.3; 128/653.4; 324/306
[58] Field of Search .......................... 128/653.1, 653.2, 128/653.3, 653.4; 324/306, 309

[56] References Cited

U.S. PATENT DOCUMENTS 5,447,156  9/1995  Dumoulin et al. .
5,479,925  1/1996  Dumoulin et al. .

Primary Examiner—Marvin M. Lateef
Assistant Examiner—Shawna J. Shaw
Attorney, Agent, or Firm—Lawrence P. Zale; Marvin Snyder

[57] ABSTRACT

A magnetic resonance (MR) active invasive device system employs a small, high-field polarizing magnet, and a large low-field magnetic resonance (MR) imaging magnet for the purpose of generating MR images of blood perfusion in tissue. A subject is positioned in a large low-field MR imaging magnet. A catheter is inserted into the patient at or near the root of a vessel supplying blood to a portion of tissue to be imaged. A fluid, intended to be used as a contrast agent is first passed through the small high-field polarizing magnet, causing a high degree of net longitudinal magnetization to be produced in the fluid. The fluid is then introduced into the subject through the catheter. Radiofrequency (RF) pulses and magnetic field is gradients are then applied to the patient as in conventional MR imaging. Since the fluid has a larger longitudinal magnetization, before the MR imaging sequence, the fluid produces a much larger MR response signal than other tissue. Images acquired during periods of time in which the fluid is flowing and not flowing are mathematically combined to give an MR image whose pixel intensity is related to the degree of tissue perfusion.

3 Claims, 3 Drawing Sheets

MAGNETIC RESONANCE (MR) PERFUSION IMAGING IN A LOW-FIELD IMAGING MAGNET

CROSS REFERENCES TO RELATED APPLICATIONS

This application is related to U.S. patent applications "Magnetic Resonance (MR) Angiography in a low-field imaging magnet" Ser. No. 08/264,283, filed Jun. 23, 1994, now U.S. Pat. No. 5,479,925, issued Jan 2, 1996; by C. Dumoulin, R. Darrow; "MAGNETIC RESONANCE (MR) ANGIOGRAPHY USING A TOROIDAL POLARIZING MAGNET AND A Low-Field Imaging Magnet" by C. Dumoulin and R. Darrow Ser. No. 08/534,998, filed Sep. 27, 1995, now U.S. Pat. No. 5,609,153, issued Mar. 11, 1997 "MAGNETIC RESONANCE (MR) ANGIOGRAPHY USING AN INTEGRATED POLARIZING AND IMAGING MAGNET" by C. Dumoulin and S. Souza Ser. No. 08/537,573, filed Oct. 2, 1995, now U.S. Pat. No. 5,603,320, issued Feb. 18, 1997; "APPARATUS AND METHODS FOR MAGNETIC RESONANCE (MR) ANGIOGRAPHY USING HYDROGEN POLARIZED AT LOW TEMPERATURES" by S. Souza and C. Dumoulin Ser. No. 08/537,571, filed Oct. 2, 1995, now U.S. Pat. No. 5,611,340, issued Mar. 18, 1997; "APPARATUS AND METHODS FOR MAGNETIC RESONANCE (MR) ANGIOGRAPHY USING FLUIDS POLARIZED AT LOW TEMPERATURES" by C. Dumoulin, S. Souza and R. Darrow Ser. No. 08/537,572, filed Oct. 2, 1995, now U.S. Pat. No. 5,626,137, issued May 6, 1997; and "APPARATUS AND METHODS FOR MAGNETIC RESONANCE (MR) IMAGING OF CAVITIES USING FLUIDS POLARIZED AT LOW TEMPERATURES" by S. Souza, C. Dumoulin, R. Darrow and H. Cline Ser. No. 08/537,574, filed Oct. 2, 1995, now U.S. Pat. No. 5,617,859, issued Apr. 8, 1997; all assigned to the present assignee, and all incorporated by reference.

BACKGROUND OF THE INVENTION

1. Field of the Invention

The present invention relates to medical imaging of blood perfusion in tissue, and more particularly concerns the use of magnetic resonance to obtain such images.

2. Description of Related Art

Imaging of blood perfusion in tissue is closely related to the imaging of blood flow in vascular structures.

Angiography, or the imaging of vascular structures, is very useful in diagnostic and therapeutic medical procedures. MR perfusion imaging is typically performed by injecting a bolus of an MR active contrast agent into the patient during an imaging session. These agents can either decrease the T1 of blood to enhance the detected MR signal (e.g. Gd-DTPA), or they can decrease the T2 of blood to attenuate the detected MR signal (e.g. iron oxide particles). As the bolus passes through the body, the enhanced (or attenuated) signal created by the bolus increases (or decreases) the signal intensity observed in perfused tissue, but not in non-perfused tissue. The degree of signal change in the observed tissue can be used to determine the degree of tissue perfusion. A major limitation of this approach, however, is that the imaging must be performed quickly to prevent errors in the perfusion measurement since contrast agent which is not taken up by the tissue on the first pass is still available to be taken up on subsequent passes of the contrast agent through the perfused tissue. A further limitation of this approach is that it can take as long as 1–2 days for the contrast agent to be cleared from the body, thus only one injection can be performed per imaging session.

In conventional MR imaging, an inhomogeneity of the static magnetic field produced by the main magnet causes distortion in the image. Therefore a main magnet having homogeneity over a large region is desirable.

Also, a stronger static magnetic field created by the main magnet yields a better signal to noise ratio, all other factors being equal. Typically, these main magnets have been constructed of a superconducting material requiring very low temperatures, and all related support apparatus. This can become very expensive.

There is also the problem of shielding a large high-field magnet. Entire shielding rooms have been constructed to reduce the& effects of the magnetic field on nearby areas and equipment.

Currently, there is a need for a system for obtaining high quality perfusion images of selected tissues without the problems incurred with a large high-field main magnet.

SUMMARY OF THE INVENTION

A fluid is passed through a small high-field polarizing magnet before it is injected into a catheter inserted in a vessel of a patient. In order to achieve maximum polarization the fluid is made to reside in the polarizing field longer than several T1 periods. The polarized fluid is then rapidly injected into the patient. MR perfusion images are created with an MR system which comprises radio-frequency and magnetic field gradient coils and a low static-field imaging magnet. The overall system requires much less power to function than a conventional high-field imaging system, and employs a simpler, less expensive static imaging magnet which may be a resistive or permanent magnet instead of a superconducting magnet.

OBJECTS OF THE INVENTION

It is an object of the present invention to provide a system for imaging perfusion in selected tissues using magnetic resonance without the need for a homogeneous high-field imaging magnet.

It is yet another object of the present invention to provide an MR perfusion imaging system which may permit multiple contrast injections during a single imaging session.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawing in which:

DETAILED DESCRIPTION OF THE INVENTION

Figure 1:
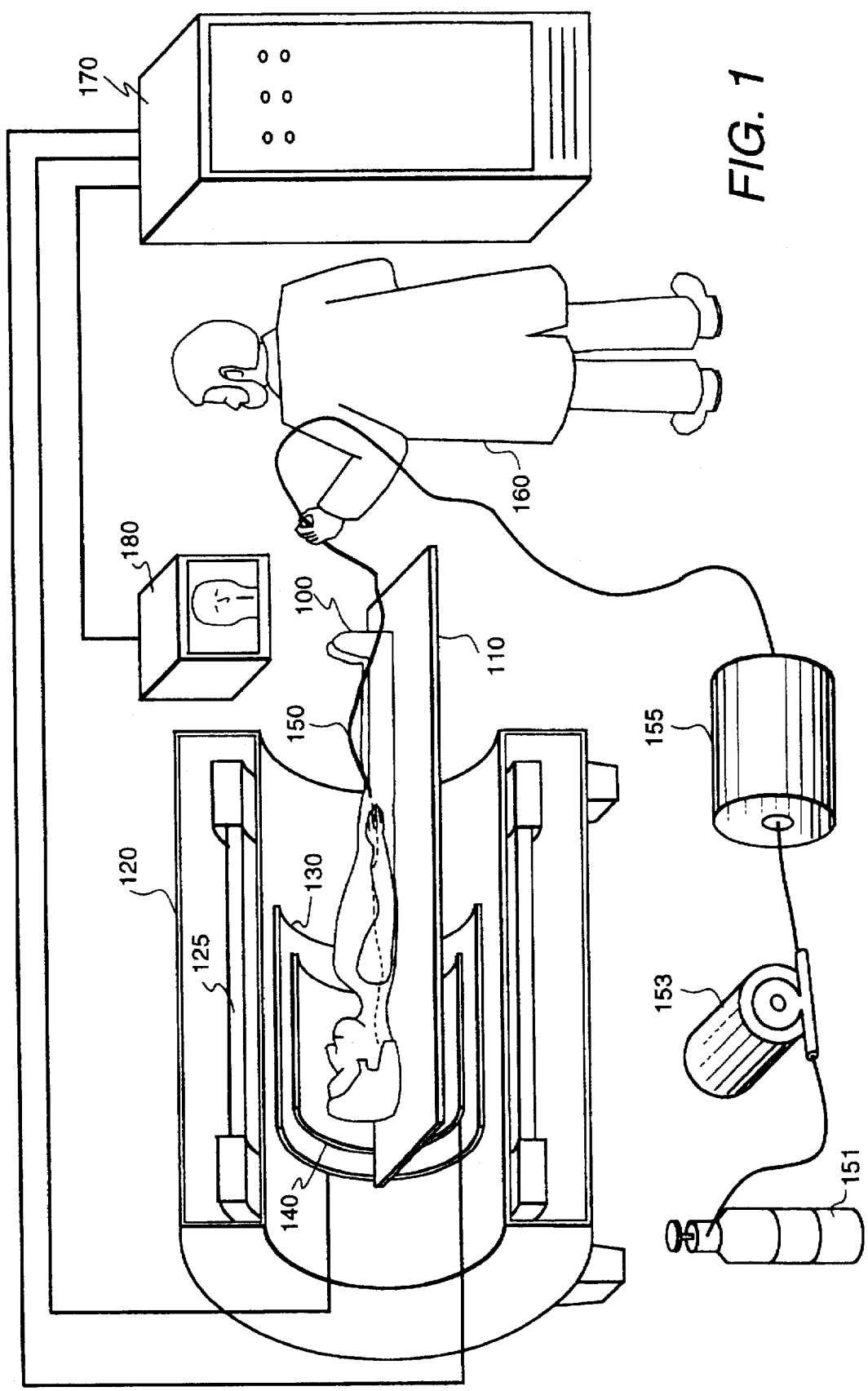
FIG. 1 is a perspective view of a first embodiment of the present invention in operation in which a perfusion image of tissue within a subject is being obtained.

In FIG. 1, a subject 100 is placed on a support table 110 and positioned in a homogeneous magnetic field generated by a magnet 125 encased in a magnet housing 120. In this embodiment, magnet 125 and magnet housing 120 have cylindrical symmetry and are shown sectioned in half to reveal the position of subject 100. A region of interest of subject 100 is located in the approximate center of the bore of magnet 125. Subject 100 is surrounded by a set of cylindrical magnetic field gradient coils 130 which create magnetic field gradients of predetermined strength at predetermined times according to predetermined MR pulse sequences, described later. Gradient coils 130 are capable of generating pulsed magnetic field gradients in three mutually orthogonal directions. At least one radio-frequency (RF) coil 140 (only one is shown in FIG. 1) also surrounds the region of interest of subject 100. In FIG. 1, RF coil 140 has a cylindrical shape with a diameter sufficient to encompass the entire subject. Other geometries, such as smaller cylinders specifically designed for imaging the head or an extremity, can be used in alternative embodiments. Non-cylindrical RF coils, such as surface coils, may also be used. RF coil 140 radiates radio-frequency energy into subject 100 at predetermined times and with sufficient power at a predetermined frequency from imaging electronics 170 so as to nutate a population of nuclear magnetic spins, hereinafter referred to as 'spins', of subject 100 in a fashion well known to those skilled in the art. RF coil 140 can also act as a receiver, detecting the MR response signals which are stimulated by nutation, if desired.

The nutation of the spins causes them to resonate at the Larmor frequency. The Larmor frequency for each spin is directly proportional to the strength of the magnetic field experienced by the spin. This field strength is the sum of the static magnetic field generated by magnet 125 and the local field generated by magnetic field gradient coil 130.

Fluid in a fluid reservoir 151 is passed through a polarizing magnet 155 by a pump 153, if required.

Polarizing magnet 155 is a superconducting magnet operating with relatively poor homogeneity, but as high a field as possible. Designs in which the field strength approaches 15 Tesla or more are possible. The magnet should be shielded to prevent stray magnetic fields from disturbing the surrounding environment. This shielding can be accomplished with an active cancellation coil surrounding the internal main coil. Since polarizing magnet 155 is not required to have a great deal of homogeneity, and because of its small size, the magnet may be considerably less expensive than existing MR imaging magnets.

The polarized fluid is then injected through catheter 150 into subject 100 where it is imaged using conventional MR imaging methods.

The fluid which is injected into the subject 100 through catheter 150 should have the highest amount of polarization possible once it reaches the capillaries. Consequently, the polarizing field of polarizing magnet 155 should be high. Also, the fluid will have to be left in the polarizing field for a period of time greater than five times the T1 of the fluid to reach full magnetization. Once the fluid leaves polarizing magnet 155 it will begin to lose polarization with a half-life equal to its T1. Consequently, it is desirable to deliver the fluid to the patient as quickly as possible. This can be done by minimizing the length of the catheter and maximizing the flow velocity.

The fluid in fluid reservoir 151 should have a T1 chosen to be as long as possible to maximize the amount of polarization delivered into the vessels of the patient. Possible choices of fluid are:

1) physiological saline solution;
2) blood previously obtained from the patient;
3) whole blood or plasma from a donor;
4) a blood substitute such as fluoridated hydrocarbons capable of carrying oxygen to tissue; and
5) blood recirculated from the patient.

The remainder of the imaging system will have the same elements as a conventional MR imaging system, however, they will function somewhat differently. A static magnetic field from a main imaging magnet, shown as 125 in FIGS. 1, 3, should be relatively low (such as 0.1 Tesla) to prevent signals from "stationary" tissue and undesired blood pools contributing to the perfusion image. A small high-field polarization magnet 155 and a large low-field main magnet, instead of a large high-field main magnet may reduce the cost of the system significantly.

Figure 3:
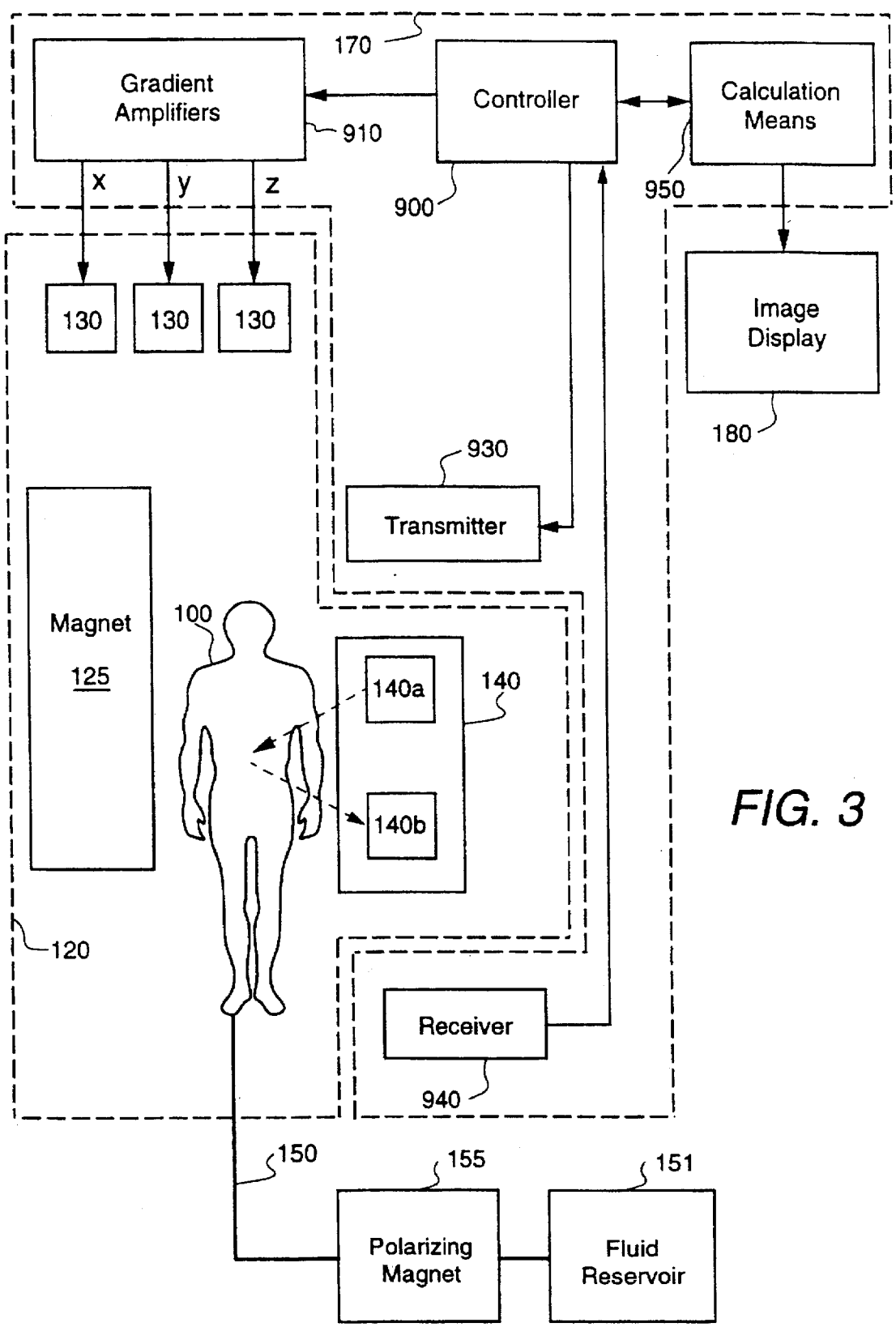
FIG. 3 is a block diagram of an MR imaging system suitable for MR perfusion imaging according to the present invention.

RF transmitter 930 and RF receiver 940 of the MR system shown in FIG. 3 would be modified to be compatible with the low-field magnet to resonate at a Larmor frequency corresponding to the strength of magnet 125 (e.g., 4.26 MHz in a 0.1 Tesla magnetic field). In an alternate embodiment, imaging magnet 125 could be an electromagnet which is driven by an amplifier similar to amplifier 910. Such a system should be able to create a pulsed homogeneous field on the order of 30 Gauss (Larmor frequency=128 kHz). Shielded gradient coil designs may be unnecessary with the present invention employing a low-field main magnet 125 (although one may still want them to prevent interference with nearby equipment).

RF transmitter 930, and RF coil 140 of the present invention perform the same functions as an RF subsystem of a conventional MR imaging device. Because the Larmor frequency is very low, however, RF coil designs having resonant frequencies comparable to the Larmor frequency will be required. At these lower frequencies, very little RF transmit power will be required, being a further advantage of the present invention.

A controller 900 provides control signals to magnetic field gradient amplifiers 910. These amplifiers drive magnetic field gradient coils 130 situated within the magnet enclosure 120. Gradient coils 130 are capable of generating magnetic field gradients in three mutually orthogonal directions.

Controller 900 generates signals which are supplied to RF transmitter 930 to generate RF pulses at one or more predetermined frequencies and with suitable power to nutate selected spins within RF coil 140 situated within the bore of magnet 125.

MR response signals are sensed by RF receive coil 140$b$ connected to receiver 940. Since the fluid from fluid reservoir 151 has passed through polarizing magnet 155, it acquires a significantly larger longitudinal magnetization, $M_L$, than 'spins' which are only subjected to low-field magnet 125. Consequently, when nutated by the RF pulses, 'spins' which have passed through polarizing magnet 155 exhibit larger transverse magnetization, $M_L$, and consequently produce a much larger MR response signal. Receiver 940 processes the MR response signals by amplifying, demodulating, filtering and digitizing. Controller 900 also collects the signals from receiver 940 and propagates them to a calculation means 950 where they are processed. Calculation means 950 applies a Fourier transformation to the signals received from controller 900 to create an MR image. The image created by calculation means 950 is displayed on an image display means 180.

Compared to conventional imaging, the MR response signal of 'spins' which did not pass through polarizing magnet 155 experience a 0.1T magnetic field, 15 times lower than that experienced by a conventional 1.5T MR imaging system. A 10T polarizing magnet 155 produces 6.67 times more polarization than a conventional 1.5T main magnet for fluid 151 which passes through polarization magnet 155. Therefore, the MR signal difference, or contrast, between polarized and non-polarized 'spins' would be on the order of 100 times.

Figure 2:
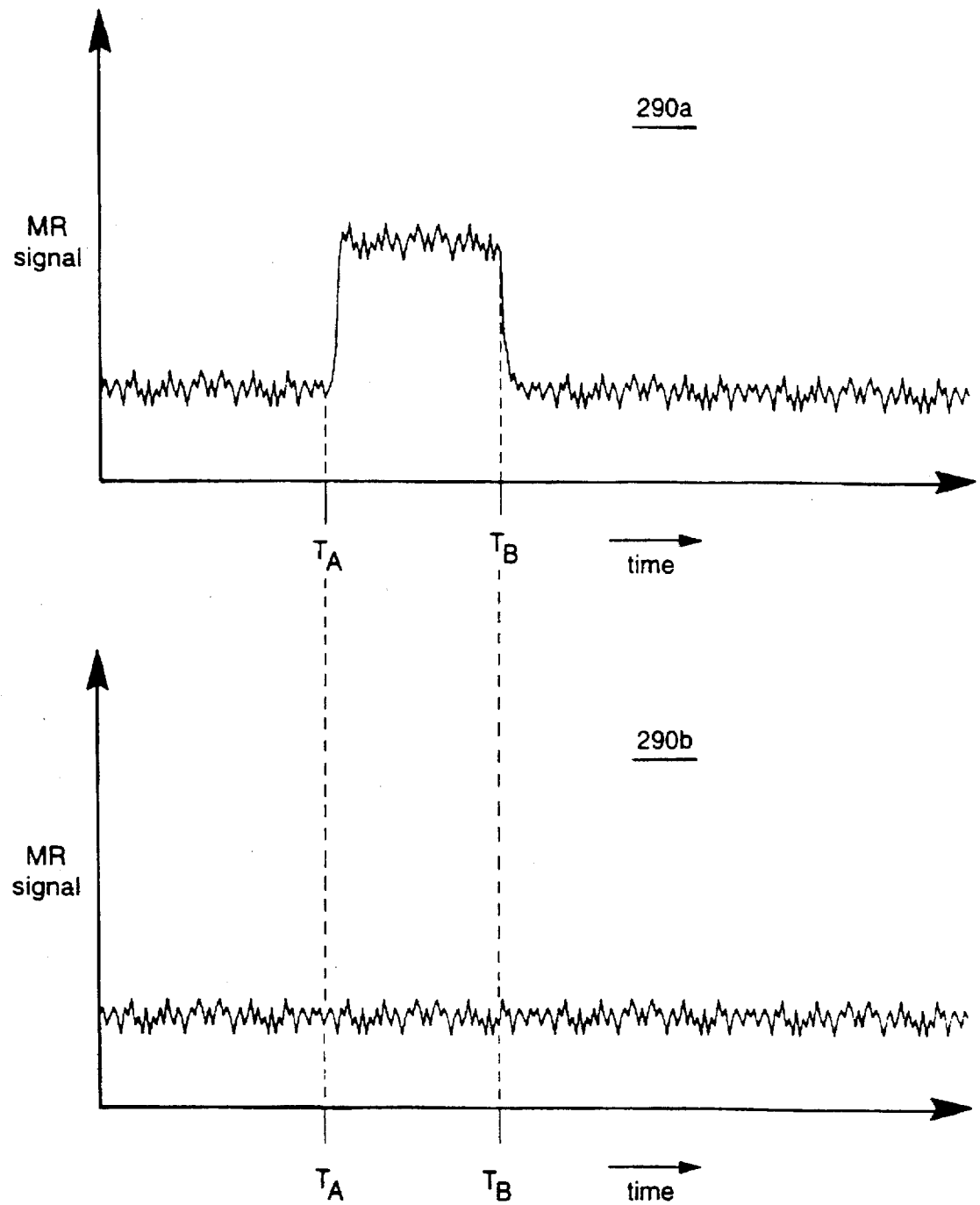
FIG. 2 is a time-course representation of MR signals from a selected portion of a subject detected with and without the injection of polarized fluid.

With the current invention perfusion images are made by acquiring a series of images with and without the polarized fluid. FIG. 2 illustrates the time course of MR signals that would be expected with a polarized fluid 290a and the time course that would be expected without a polarized fluid 290b. In FIG. 2, the injection of polarized fluid begins at time $T_A$ and ends a time $T_B$. If no injection is made (or if an injection is made with fluid having the same degree of polarization present in the rest of the body) no signal changes are observed. Note that it is also possible to inject a fluid which has no polarization. In this case the MR signal during the interval $T_A$ to $T_B$ will decrease. Perfusion images are made by mathematically combining MR image data acquired in the presence and absence of polarized fluid flow. A simple such mathematical operation is the computation of difference image by taking a pixel-by-pixel difference between the two acquired images to result in each pixel value of the corresponding pixel in the perfusion image.

One useful aspect of the present invention is that the degree of MR signal enhancement is determined only by fluid passing through the tissue for the first time. This is because the high degree of polarization created by polarizing magnet 155 is lost with a half-life of T1 in the fluid. Consequently, for fluids having a T1 less than a few seconds, the high polarization induced by polarizing magnet 155 has disappeared by the time the fluid has made its first pass through the subject's vascular system. A perfusion image created with only first pass changes in MR signal intensity will provide a more reliable assessment of tissue perfusion.

The MR system outlined in FIG. 3 may also be used for the generation of conventional MR images in a manner well known to those skilled in the art. Received MR response signals are detected with either the same RF coil used by the transmitter or a surface coil independent of the coil driven by the transmitter.

It should be noted that the polarizing methods described in patent applications: "APPARATUS AND METHODS FOR MAGNETIC RESONANCE (MR) ANGIOGRAPHY USING HYDROGEN POLARIZED AT LOW TEMPERATURES" by S. Souza and C. Dumoulin Ser. No. 08/537,571, filed Oct. 2, 1995, now U.S. Pat. No. 5,611,340, issued Mar. 18, 1997; and "APPARATUS AND METHODS FOR MAGNETIC RESONANCE (MR) ANGIOGRAPHY USING FLUIDS POLARIZED AT LOW TEMPERATURES" by. C. Dumoulin, S. Souza and R. Darrow Ser. No. 08/537,572, filed Oct. 2, 1995, now U.S. Pat. No. 5,626,137, issued May 6, 1997; in which additional degrees of polarization are achieved can be advantageously used with the present invention.

While several presently preferred embodiments of the novel MR perfusion imaging system have been described in detail herein, many modifications and variations will now become apparent to those skilled in the art. It is, therefore, to be understood that the appended claims are intended to cover all such modifications and variations as fall within the true spirit of the invention.

What is claimed is:

1. A method of obtaining magnetic resonance (MR) perfusion images from a subject comprising:

a) applying a substantially homogeneous magnetic field over said subject;

b) polarizing a contrast fluid to create longitudinal magnetization, by passing it through a high-field polarizing magnet;

c) routing the polarized contrast fluid from the polarizing magnet into a selected vessel of said subject at selected times;

d) transmitting RF energy into said subject of a selected duration, amplitude and frequency to cause nutation of the contrast fluid and other tissue within said subject;

e) varying the amplitude of the magnetic field in at least one spatial dimension over time;

f) detecting a set of MR response signals from said subject during a first period of time in which contrast fluid is injected into said subject;

g) detecting a set of MR response signals from said subject during a second period of time in which contrast fluid is not injected into said subject;

h) calculating a perfusion image from the detected MR response signals by mathematically combining signals detected during the first period of time with signals detected during the second period of time; and i) displaying the calculated perfusion image to an operator.

2. The method of obtaining magnetic resonance (MR) perfusion images of claim 1 wherein the step of calculating a perfusion image comprises subtracting the MR response signal of the second set from the MR response signal of the first set for each corresponding location to result in a perfusion image.

3. The method of obtaining magnetic resonance (MR) perfusion images of claim 1 wherein the contrast fluid is passed through the polarizing magnet in the absence of a radiofrequency (RF) excitation pulse.

* * * * *